United States Patent [19]

Ishizaka et al.

[11] Patent Number: 4,751,377
[45] Date of Patent: Jun. 14, 1988

[54] LIGHT BEAM SCANNING RECORDING APPARATUS AND METHOD OF CORRECTING INTENSITY OF IMAGE TO BE RECORDED THEREBY

[75] Inventors: Hideo Ishizaka; Yuji Ohara, both of Kanagawa, Japan

[73] Assignee: Fuji Photo Film Co., Ltd., Japan

[21] Appl. No.: 947,221

[22] Filed: Dec. 29, 1986

[30] Foreign Application Priority Data

Jun. 13, 1986 [JP] Japan ............... 61-137663

[51] Int. Cl.$^4$ ............................................. G01J 1/35
[52] U.S. Cl. .................................... 250/205; 250/234; 355/67; 358/293
[58] Field of Search ............... 250/205, 234, 235, 236; 355/67, 68, 69; 358/293, 294

[56] References Cited

U.S. PATENT DOCUMENTS

| | | | |
|---|---|---|---|
| 4,352,553 | 10/1982 | Hirahara | 250/205 |
| 4,544,258 | 10/1985 | Takano | 355/68 |
| 4,602,156 | 7/1986 | Asai et al. | 250/327.2 |
| 4,651,226 | 3/1987 | Motoori et al. | 358/293 |
| 4,653,904 | 3/1987 | Imamura | 355/68 |

*Primary Examiner*—Edward P. Westin
*Assistant Examiner*—Jessica L. Ruoff

[57] ABSTRACT

In a light beam scanning recording apparatus, a light beam is modulated by a modulator according to image signals and is caused to scan a photosensitive recording material, and the recording material is developed. The apparatus is provided with a signal converting section which converts image signals to be input into the modulator according to a predetermined conversion table so that desired image densities can be obtained on the recording material, a test pattern signal generating section which generates test pattern signals bearing thereon different image densities and inputs them into the modulator, an image density measuring system which measures the image densities of the test pattern on the recording material developed after scanning by a light beam modulated according to the test pattern signals, and a conversion table making section which determines, on the basis of the relation between the test pattern signals and the image densities of the test pattern measured by the image density measuring system and desired image signal-image density characteristics, the image signals corresponding to the image densities obtained by the respective test pattern signals referring to the desired image signal-image density characteristics, thereby obtaining the relation between the image signals and the test pattern signals, and makes the conversion table on the basis of the relation between the image signals and the test pattern signal.

4 Claims, 4 Drawing Sheets

LIGHT BEAM SCANNING RECORDING APPARATUS AND METHOD OF CORRECTING INTENSITY OF IMAGE TO BE RECORDED THEREBY

BACKGROUND OF THE INVENTION

1. Field of the Invention

This invention relates to a light beam scanning recording apparatus in which a light beam modulated according to image signals is caused to scan a photosensitive material to record thereon the image born by the image signals, and a method of correcting the intensity of the image to be recorded.

2. Description of the Prior Art

There has been known a light beam scanning recording apparatus in which a light beam is modulated according to image signals representing an image to be recorded, and the modulated light beam is caused to scan a photosensitive material, and the photosensitive recording material is developed. In such light beam scanning recording apparatuses, images recorded on the recording material using the same image signals can differ in intensity due to fluctuation in the developing conditions of the recording material (e.g., the developing temperature and properties of the developing solution), or individual variation of the recording materials and the recording mechanisms such as individual variation of the semiconductor laser and that of the transmissivity of the optical system. Particularly, in the case of diagnostic images in which high gradation is necessary, the fluctuation in the image density can adversely affect diagnostic performance.

SUMMARY OF THE INVENTION

In view of the foregoing observations and description, the primary object of the present invention is to provide an improved light beam scanning recording apparatus which can record images with constant image densities irrespective of fluctuation in the factors described above.

Another object of the present invention is to provide a method of correcting the intensity of the image to be recorded which enables the image to be recorded with constant intensity irrespective of fluctuation in the factors described above.

The light beam scanning recording apparatus in accordance with the present invention is characterized by having a signal converting section which converts image signals to be input into the modulator according to a predetermined conversion table so that desired image densities can be obtained on the recording material, a test pattern signal generating section which generates test pattern signals bearing thereon different image densities and inputs them into the modulator, an image density measuring system which measures the image densities of the test pattern on the recording material developed after scanning by a light beam modulated according to the test pattern signals, and a conversion table making section which determines, on the basis of the relation between the test pattern signals and the image densities of the test pattern measured by the image density measuring system and desired image signal-image density characteristics, the image signals corresponding to the image density obtained by the respective test pattern signals referring to the desired image signal-image density characteristics, thereby obtaining the relation between the image signals and the test pattern signals, and makes the conversion table on the basis of the relation between the image signals and the test pattern signal.

DESCRIPTION OF THE PREFERRED EMBODIMENT

Figure 1:
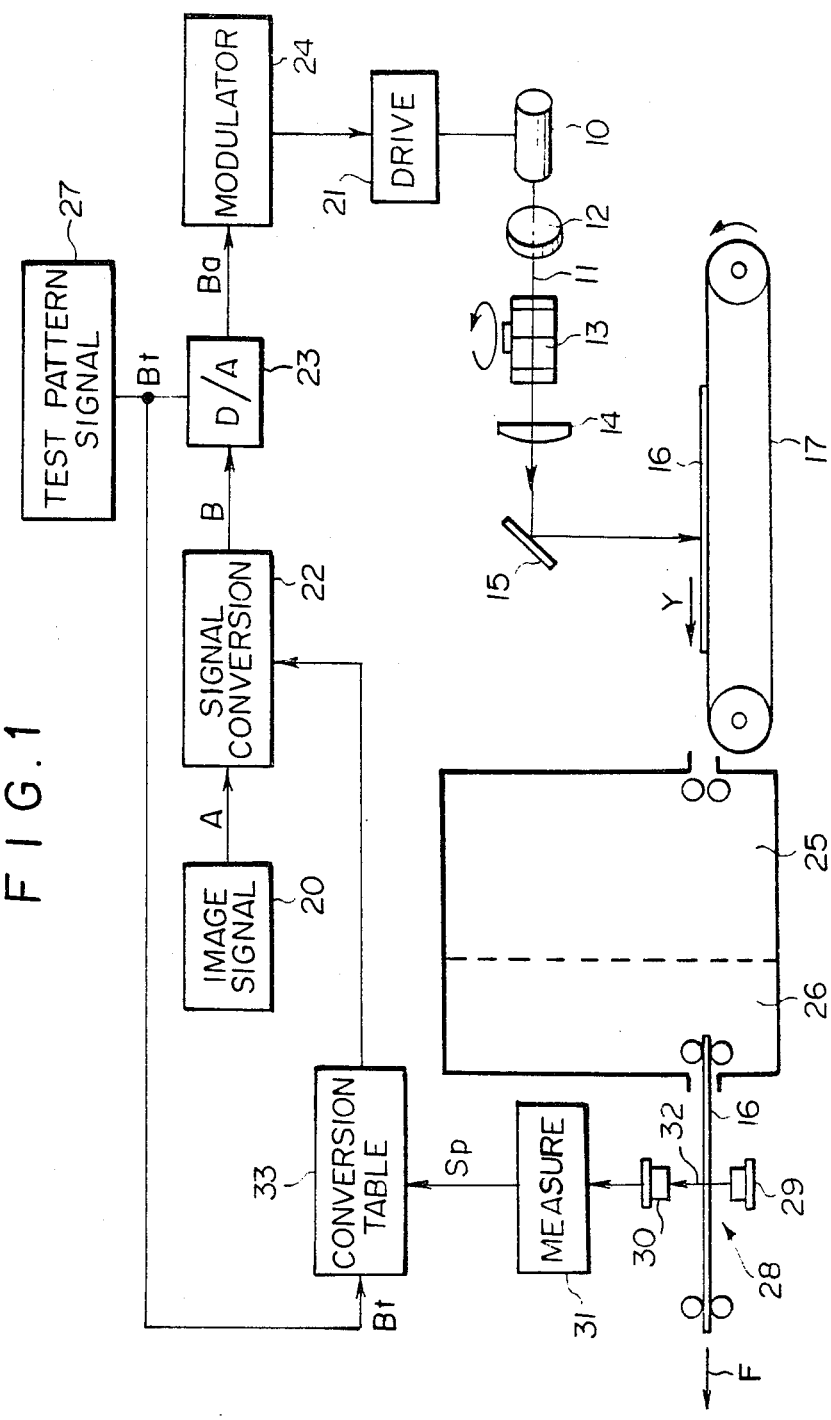
FIG. 1 is a schematic view showing a light beam scanning recording apparatus in accordance with an embodiment of the present invention.

In FIG. 1, a light beam 11 emitted from a semiconductor laser 10 is collimated by a collimator lens 12, and the collimated light beam 11 impinges upon a light deflector 13 which may be a rotating polygonal mirror, for instance. The collimated light 11 is deflected by the deflector 13 to travel through a converging lens 14 which generally consists of an f.θ lens, and is reflected by an elongated mirror 15 to scan the surface of a photosensitive recording material 16 in the direction perpendicular to the direction of arrow Y (main scanning). At the same time, the recording material 16 is fed in the direction of the arrow Y (sub-scanning) by a feeding mechanism 17 which may comprise an endless belt, for instance. Thus, the light beam 11 two-dimensionally scans the surface of the recording material 16. The light beam 11 is modulated, as emitted from the laser 10, according to image signals A output from an image signal output device 20, and accordingly, an image (latent image) born by the image signals A is recorded on the photosensitive recording material 16. The image signals A are digital signals and are converted into signals B by a signal converting section 22 on the basis of a predetermined conversion table as will be described in detail later. The signals B are further converted into analogue signals Ba by a D/A converter 23 and then the analogue signals Ba are input into a modulator 24. The modulator 24 controls a driver 21 for the semiconductor laser 10 according to the analogue image signals Ba, thereby modulating the light beam 11 emitted from the laser 10.

After recording of the image on the photosensitive recording material 16, the recording material 16 is fed to an automatic developing system 25 to be developed thereby, and then discharged through a drying section 26. On the developed recording material 16, the image born by the image signals A is recorded as a visual image.

As mentioned above, images recorded on the recording material using the same image signals can differ in intensity due to fluctuation in the developing conditions in the automatic developing system 25, individual variation of the recording materials 16, individual variation of the semiconductor laser 10 or individual variation of transmissivity of the optical system, e.g. the converging lens 14. This problem is avoided in the following manner in this embodiment.

Test pattern signals Bt are input into the D/A converter 23 from a test pattern signal generator 27. The test pattern signals Bt are for recording a test pattern comprising, for instance, sixteen spots having different image densities in predetermined positions on the surface of the recording material 16, and are input into the D/A converter 23 prior to recording of the image born by the image signals A output from the image signal output device 20. After the test pattern is recorded on the recording material 16 according to the test pattern signal Bt, the recording material 16 is developed and dried. Then, the image densities of the respective spots of the test pattern on the recording material 16 are measured by an image density measuring system 28 disposed downstream of the drying section 26. The image density measuring system 28 comprises a light source 29, e.g., a light emitting diode, a light detector 30, e.g., a photo transistor, and a measuring circuit 31 which receives the output of the light detector 30, and measures the densities of the respective spots of the test pattern by way of the intensities of the light 32 emitted from the light source 29 and transmitted through the respective spots. The measuring circuit 31 delivers test pattern intensity signals Sp representing the intensities of the spots of the test pattern to a conversion table making section 33. Generally, the intensities of the spots are measured while the recording material 16 is fed in the direction of arrow F in FIG. 1, and accordingly, the spots are generally recorded in a row extending in the direction of the arrow F. The conversion table making section 33 makes a conversion table T according to which the image signals A are converted into the signals B by the signal converting section 22, and delivers it to the signal converting section 22. The conversion table T is made in the following manner.

Figure 2:
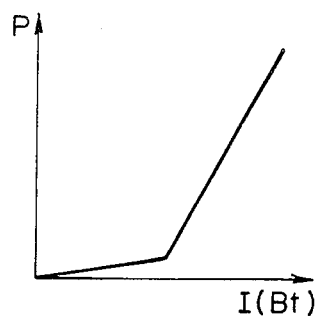
FIG. 2 is a graph showing the relation between the driving current of a semiconductor laser and the light output of the same.
Figure 3:
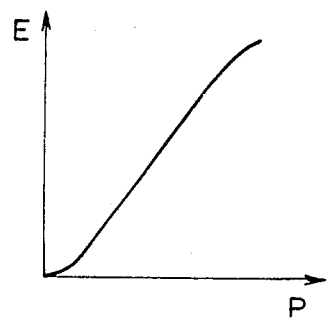
FIG. 3 is a graph showing the relation between the laser beam output and the energy density.
Figure 4:
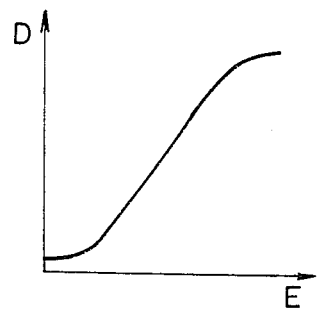
FIG. 4 is a graph showing the relation between the energy density of the laser beam and the image density.

The conversion table making section 33 determines the actual relation between the test pattern signal Bt and the measured image densities D of the spots of the test pattern recorded. As is well known, the relation between the driving current I of the semiconductor laser 10 and the light output P of the same is substantially as shown in FIG. 2. The driving current I is controlled by the modulator 24 in proportion to the test pattern signals Bt, and accordingly, the relation shown in FIG. 2 represents the relation between the test pattern signals Bt and the light output P. The relation between the light output P and the energy density E of the light beam 11 which determines the image density on the recording material 16 is substantially as shown in FIG. 3. Further, the gradient properties of normal photosensitive recording material 16, that is, the relation between the energy density E and the image density D is substantially as shown in FIG. 4. Accordingly, the actual relation between the test pattern signals Bt and the measured image densities D of the spots of the test pattern recorded obtained by the conversion table making section 33 will be substantially as shown in the first quadrant of FIG. 5. Further, there is stored in the conversion table making section 33 desired image signal-image density characteristics, i.e., a desired relation between the image signals A and the image density D on the recording material 16 (the second quadrant in FIG. 5), and the conversion table making section 33 makes the conversion table T on the basis of the actual relation between the test pattern signal Bt and the measured image densities D of the spots of the test pattern recorded. That is, the conversion table making section 33 determines the image signals A corresponding to the image densities D obtained by the respective test pattern signals Bt referring to the desired image signal-image density characteristics, thereby finally obtaining the relation between the image signals A and the test pattern signals Bt (shown in the fourth quadrant in FIG. 5). The relation between the image signals A and the test pattern signals Bt can be continuously obtained, for instance, by interpolation after determining the relation between the image signals A and the test pattern signals Bt actually used in formation of the test pattern, for instance, sixteen test pattern signals Bt. The conversion table making section 33 makes the conversion table T on the basis of the relation f between the image signals A and the test pattern signals Bt and delivers the conversion table T thus made to the signal converting section 22.

Figure 5:
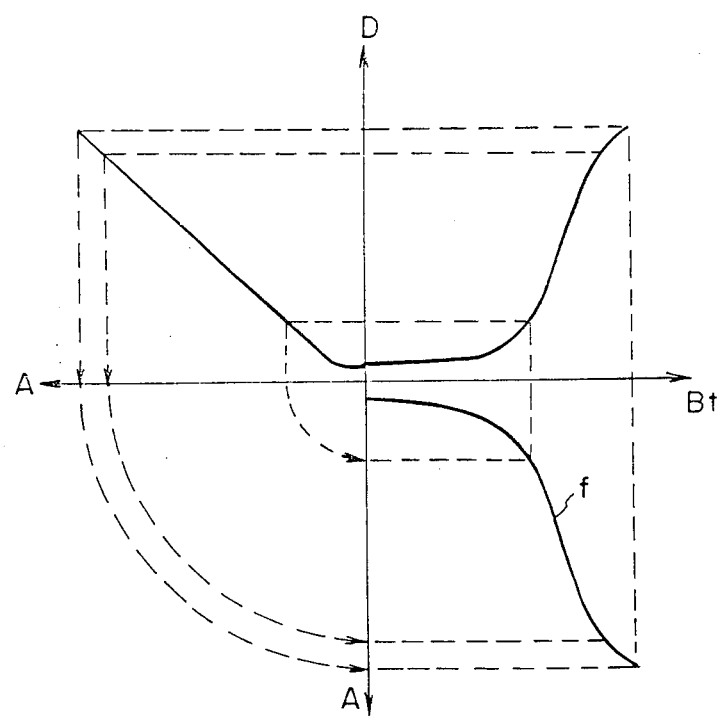
FIG. 5 is a view for illustrating the manner of making the conversion table.

When the image signals A are converted into the signals B according to the conversion table T made in the manner described above before recording the image born by the image signals A from the image signal output device 20 on the photosensitive recording material 16, the relation between the image signals A and the image densities D on the recording material 16 proves to be the desired relation shown in the second quadrant in FIG. 5.

As described above, the relations shown in FIGS. 2, 3 and 4 can change due to variance among individual semiconductor lasers 10 and/or the recording materials 16, fluctuation in the developing conditions and the like, and accordingly the relation between the test pattern signals Bt and the image densities D shown in FIG. 5 can change. However, even if the relation between the test pattern signals Bt and the image densities D on the recording material 16 changes, an image can be recorded on the recording material 16 according to the desired relation between the image signals A and the image densities on the recording material 16 by making the conversion table T on the basis of the changed relation between the test pattern signals Bt and the image densities D on the recording material 16 and the desired image signal image density characteristics shown in the second quadrant in FIG. 5. Accordingly, by remaking the conversion table T when it is expected that the factors which can affect the image densities D on the recording material 16 changes, images having a desired intensity can be constantly obtained.

As described above the spots of the test pattern are generally recorded on the recording material 16 in a row extending in the direction of the arrow F and the intensities of the spots are measured successively while the recording material 16 is fed in the direction of the arrow F. In this case, when the feeding speed of the recording material 16 fluctuates during measurement of the intensities of the spots due to fluctuation in the supply voltage, there arises a fear that the intensity of the spot corresponding to each test pattern signal Bt is mistaken for that corresponding to a different test pattern signal Bt, making of the conversion table is adversely affected.

Figure 6:
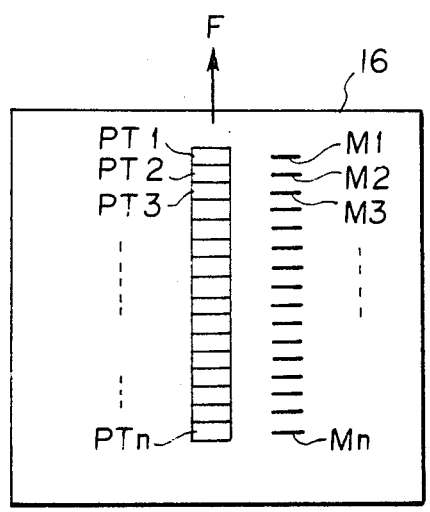
FIG. 6 is a view showing the positions of test pattern spots and position reference marks on a recording medium.
Figure 7:
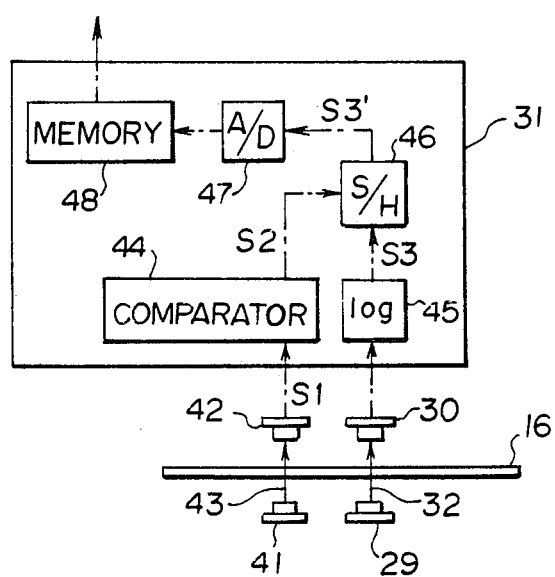
FIG. 7 is a schematic view of an alternate embodiment of the present invention showing a measuring circuit and an image density measuring system of a light beam scanning recording apparatus.

Another embodiment of the present invention in which such a problem can be avoided will be described with reference to FIGS. 6 and 7, hereinbelow. This embodiment is substantially the same as the embodiment described above except the manner of recording the test pattern and measuring the intensities of the respective spots of the test pattern, and accordingly, the difference therebetween will be mainly described, hereinbelow.

In this embodiment, the test pattern signals Bt generated from the test pattern signal generating section 27 bear also position reference marks. That is, as shown in FIG. 6, according to the test pattern signals Bt, test pattern spots PT1 to PTn having different image densities are recorded on the recording material 16 in a row extending in the direction of the arrow F in which the recording material 16 is fed, and at the same time, position reference marks M1 to Mn are recorded on the recording material 16 respectively in alignment with the test pattern spots PT1 to PTn in the direction perpendicular to the direction of the arrow F and in a row parallel to the row of the test pattern spots PT1 to PTn.

In this embodiment, the image density measuring system 28 includes, in addition to the light source 29 and the photo detector 30 for measuring the intensities of the test pattern spots, a light source 41 and a photo detector 42 for detecting the position reference marks M1 to Mn. The light source 41 and the photo detector 42 are disposed respectively in alignment with the light source 29 and the photo detector 30 for measuring the intensities in the direction perpendicular to the direction of the arrow F. The intensity of mark detecting light 43 emitted from the light source 41 is received by the photo detector 42. The output of the photo detector 42 is input into a comparator 44 of the measuring circuit 31 which, in this embodiment, comprises the comparator 44, a logarithmic amplifier 45, a sample hold circuit 46, an A/D converter 47 and a memory 48. The comparator 44 compares the output S1 of the photo detector 42 with a predetermined reference signal, and when the former becomes lower than the latter, the comparator 44 generates a sampling timing signal S2. The output S1 of the photo detector 42 becomes lower than the reference signal when one of the position reference marks M1 to Mn intervenes between the light source 41 and the photo detector 42, and accordingly, the sampling timing signal S2 is generated each time one of the marks M1 to Mn crosses the optical path of the mark detecting light 43.

The sampling timing signal S2 is input into the sample hold circuit 46. Into the sample hold circuit 46 is continuously input the analogous output S3 (pattern intensity signal) of the photo detector 30 amplified and log-converted by the logarithmic amplifier 45, and the sample hold circuit 46 sample-holds the analogous output S3 upon receipt of the sampling timing signal S2. The output S3' held by the sample hold circuit 46 is digitalized by the A/D converter 47 and is stored in the memory 48. Thus, the intensity signals S3' are successively stored in the memory 48 each time one of the marks M1 to Mn crosses the optical path of the mark detecting light 43. The memory 48 stores these outputs S3' at first to n-th addresses in the order of input. By sample-holding the intensity signals at the moments one of the marks M1 to Mn is detected, the intensity signals precisely representing the intensities of the respective test pattern spots PT1 to PTn can be constantly obtained irrespective of fluctuation in the feeding speed of the recording material 16.

After all the test pattern spots PT1 to PTn are passed through the image density measuring system 28, the conversion table making section 33 reads out the intensity signals S3' stored in the memory 48 in the order of the addresses and makes the conversion table T.

Though in the embodiment described above, each of the position reference marks is disposed in alignment with the corresponding test pattern spot in the direction perpendicular to the feeding direction of the recording material 16, in the case that it is difficult to arrange the photo detectors 30 and 42 in alignment with each other in the direction perpendicular to the feeding direction of the recording material 16, the photo detectors 30 and 42 may be displaced from each other in the feeding direction of the recording material 16 with the row of the test pattern spots PT1 to PTn and the row of the position reference marks M1 to Mn being displaced from each other in the feeding direction of the recording material 16.

We claim:

1. A light beam scanning recording apparatus in which a light beam is modulated by a modulator according to image signals and is caused to scan a photosensitive recording material, and the recording material is developed, characterized by having a signal converting section which converts the image signals to be input into the modulator according to a predetermined conversion table so that desired image densities can be obtained on the recording material, a test pattern signal generating section which generates test pattern signals bearing thereon different image densities and inputs them into the modulator, an image density measuring system which measures the image densities of the test pattern on the recording material developed after scanning by a light beam modulated according to the test pattern signals, and a conversion table making section which determines, on the basis of the relation between the test pattern signals and the image densities of the test pattern measured by the image density measuring system and desired image signal-image density characteristics, the image signals corresponding to the image densities obtained by the respective test pattern signals referring to the desired image signal-image density characteristics, thereby obtaining the relation between the image signals and the test pattern signals, and makes the conversion table on the basis of the relation between the image signals and the test pattern signal.

2. A light beam scanning recording apparatus as defined in claim 1 in which said image density measuring system measures the image densities while the recording material is fed, and said test pattern comprises a plurality of spots which have different image densities and arranged in a row extending in the feeding direction of the recording material.

3. A light beam scanning recording apparatus as defined in claim 2 in which a position reference mark is recorded on the recording material in a position corresponding to one of the spots of the test pattern, and the image intensity measuring system adopts the intensity upon detection of the position reference mark as the intensity of the spot of the test pattern corresponding to the position reference mark.

4. In a light beam scanning recording apparatus in which a light beam is modulated by a modulator according to image signals and is caused to scan a photosensitive recording material, and the recording material is developed, a method of correcting the intensity of the image to be recorded comprising steps of converting the image signals to be input into the modulator according to a predetermined conversion table, measuring the image densities of a plurality of test pattern spots recorded in a row on the recording material, and correcting the conversion table on the basis of the result of the measurement, wherein the improvement comprises steps of recording position reference marks in a row in positions respectively corresponding to the test pattern spots, measuring the image densities of the test pattern spots while the recording material is fed in the direction of the row of the test pattern spots, detecting the position reference marks, and adopting the intensity upon detection of the position reference mark as the intensity of the test pattern spot corresponding to the position reference mark.

* * * * *

UNITED STATES PATENT AND TRADEMARK OFFICE
CERTIFICATE OF CORRECTION

PATENT NO. : 4,751,377

DATED : June 14, 1988

INVENTOR(S) : Hideo Ishizaka, Yuji Ohara

It is certified that error appears in the above-identified patent and that said Letters Patent is hereby corrected as shown below:

Title page:

[30]    Foreign Application Priority Data

Dec. 27, 1985 [JP]    Japan..........60-299849

June 13, 1986 [JP]    Japan..........61-137663

Signed and Sealed this

Thirteenth Day of December, 1988

Attest:

DONALD J. QUIGG

*Attesting Officer*    *Commissioner of Patents and Trademarks*